United States Patent [19]

Mehta

[11] Patent Number: 4,792,640

[45] Date of Patent: Dec. 20, 1988

[54] HYDROCARBYLOXY MAGNESIUM HALIDES

[75] Inventor: Vijay C. Mehta, Gastonia, N.C.

[73] Assignee: Lithium Corporation of America, Gastonia, N.C.

[21] Appl. No.: 25,416

[22] Filed: Mar. 13, 1987

Related U.S. Application Data

[63] Continuation-in-part of Ser. No. 853,496, Apr. 18, 1986.

[51] Int. Cl.$^4$ .............................................. C07C 31/30
[52] U.S. Cl. ...................................... 568/851; 568/902
[58] Field of Search ................ 568/851, 902; 260/413; 556/480; 502/111

[56] References Cited

U.S. PATENT DOCUMENTS

| | | | |
|---|---|---|---|
| 3,439,042 | 4/1969 | Eschinasis | 568/851 |
| 3,920,713 | 11/1975 | Feichtinger | 568/851 |
| 4,133,824 | 1/1979 | Malpass | 568/851 |
| 4,178,300 | 12/1979 | van den Berg | 568/851 |
| 4,220,554 | 9/1980 | Scata et al. | 252/429 |
| 4,370,257 | 1/1983 | Imai et al. | 252/429 |
| 4,451,688 | 5/1984 | Kuroda et al. | 585/524 |

OTHER PUBLICATIONS

Turova et al., "Journal of Organometallic Chemistry", vol. 42 (1972), pp. 9–16.

*Primary Examiner*—Werren B. Lone
*Attorney, Agent, or Firm*—Charles C. Fellows; Eugene G. Seems

[57] ABSTRACT

This invention concerns solid organometallic hydrocarbyloxymagnesium halides of the formula ROMgX wherein RO is a hydrocarbyloxy group of 1 to 20 carbon atoms and X is halide, and a two step process for making these halides comprising:

(a) reacting an activated magnesium metal with an alkyl halide of the formula R'X, in which R' is compound containing 1 to 20 carbon atoms, in a dry inert hydrocarbon media, under a dry inert atmosphere to produce a compound of the formula R'MgX in which R' and X have the meanings ascribed to them herein; and, (b) and reacting the R'MgX compound with an oxygen containing compound, containing 1 to 20 carbon atoms, selected from the group consisting of alcohols, ketones, aldehydes and esters to produce the compound ROMgX.

When the oxygen containing compound is 2-alkyl substituted, the products are hydrocarbon soluble.

24 Claims, No Drawings

HYDROCARBYLOXY MAGNESIUM HALIDES

This application is a continuation-in-part of my earlier copending application Serial No. 853,496 filed April 18, 1986.

This invention concerns novel hydrocarbyloxy magnesium halides, methods of making them and their use in making supports for the supported type Ziegler-Natta (Z/N) olefin polymerization catalyst.

Ziegler-Natta type catalysts have been employed for many years in the production of polyolefins. Many attempts have been made to obtain catalysts with higher and higher activity at high stereospecificity. Supported catalysts, particularly titanium supported on various carriers, very frequently a magnesium compound, have been developed. These supported catalysts greatly increase the ability of the titanium to polymerize olefins as compared with conventional Ziegler-Natta type catalysts. Nevertheless, the ultimate catalyst has not yet been perfected.

A great deal of research has therefore gone into making supported catalysts having a magnesium compound, such as magnesium chloride, to serve as a support or carrier for the titanium. Grignard agents of the formula RMgX in ether provide attractive appearing starting materials for making compounds of the formula ROMgX. Unfortunately, it is very difficult to remove all of the ether and while some olefin polymerizers don't want any ether present in their polymerizations it is acceptable to others.

R.E. Dietz in U.S. Pat. No. 4238354 disclosed a method for preparing a catalyst composition by mixing a milled mixture of magnesium and particulate inorganic solid selected from magnesium halides such as magnesium chloride with an alcohol to form an unagglomerated product, the alcohol being in a quantity as stoichiometrically required to convert the magnesium to a magnesium dialkoxide. This product was then contacted with titanium tetrachloride to form a catalyst from which excess titanium was washed with an inert solvent.

Masafumi Imai, et al., in U.S. Pat. No. 4370257 disclosed a process for preparing a magnesium containing solid product represented by the formula R'OMgX by reacting magnesium metal, which had been preactivated by heating in a solvent, with a halogenated hydrocarbon represented by the formula RX wherein R can be an alkyl, aryl or cycloalkyl group having one to about 20 carbon atoms and X is a halogen atom, and a compound represented by the formula X' C(OR')hd 4-m wherein X' can be a hydrogen atom, a halogen atom, an alkyl, aryl, cycloalkyl group having from about one to about ten carbon atoms or a halogenated alkyl, aryl, or cycloalkyl group, R' can be an alkyl or cycloalkyl group having from about 1 to about 20 carbon atoms and M is 0, 1 or 2. Methyl iodide was used as a reaction promoter.

Masahiko Kuramoto in Japanese Kokai Sho No. 57-151601 disclosed a method of olefin polymerization using a catalyst made from the reaction product of magnesium metal, a halide hydrocarbon an an alcohol. The magnesium metal, halide hydrocarbon and alcohol were mixed together in a molar ratio of 1:0.1 to 10:0.1 to 2, respectively and reacted in heptane or hexane.

An article by N. Ya. Turova and E.P. Turevskaya entitled Alkoxymagnesium Halides, Journal of Organometallic Chemistry 42 (1972), pp 9–17, discusses formation of several alkoxymagnesium halides by the thermolysis of cements and "from the alcoholysis of solutions of Grignard reagents in ether." This article notes that when an alcohol is treated with a two fold excess of "ether-free RMgHal in hydrocarbon solvent the result of the reaction is the formation of soluble RMgOR' which is stable to active hydrogen. Although the data of Turova and Turevskaya confirm formation of XMgOR' from alcohol and RMgX in ether they noted that "The interaction of an alcohol with RMgHal in ether may however differ from that in a hydrocarbon solvent."

There has been much investigation into catalyst supports containing magnesium and a halide. Some investigators have made supports from magnesium alkyls, and halide reactants but the art is lacking true organometallic alkoxymagnesium halides desirably some of which are low melting and/or soluble materials.

The present invention provides a process for making organometallic hydrocarbyloxymagnesium halides of the formula ROMgX in which RO is a hydrocarbyloxy group having 1 to 20 carbon atoms and X is a halide, preferably chloride. An alkylmagnesium, halide is reacted with an oxygen containing compound, such as an alcohol, of 1 to 20 carbon atoms to produce the hydrocarbyloxy magnesium halide in an inert hydrocarbon medium. The alkylmagnesium halide can be made by reacting magnesium metal, preferably activated with iodine, with an alkyl halide in a hydrocarbon solvent to produce the alkylmagnesium halide as a solid reaction product. This reaction product may also be called a complex, that is dialkylmagnesium complexed with magnesiumdihalide. The process can be and is preferably conducted as a two step process in which the alkylmagnesium halide is produced in a hydrocarbon solvent and then reacted with an oxygen containing compound to produce the hydrocarbyloxy magnesium halide.

The reactions are conveniently conducted under anhydrous conditions using a blanket of inert gas, usually nitrogen or argon, in an inert, aprotic solvent, usually an inert hydrocarbon solvent, preferably atmospheric pressure and reflux of the solvent but higher and lower temperatures (40° C. to 200° C.) can be used.

The term hydrocarbyloxy as used herein refers to a radical 'OR', a monovalent oxyhydrocarbon group such as alkoxy, cycloalkoxy, aryloxy, aralkoxy and similar oxyhydrocarbon groups derived from an alkyl, cycloalkyl, alkylaryl or arylalkyl alcohol ketone, aldehyde or ester containing 1 to 20 atoms. These alcohols, ketones, aldehydes or are referred to herein as oxygen containing compounds. Most typically the oxygen containing used in this invention is a monohydric alkanol, cycloalkanol or aromatic alcohol, ROH, in which R is a hydrocarbon radical having 1–18 carbon atoms.

Unsubstituted primary monohydric alcohols or alkanols ($C_l$ to $C_{20}$), which are reacted with alkylmagnesium halide compounds in various of the embodiments of this invention are exemplified by methanol, ethanol, propanol, butanol, pentanol, hexyl alcohol, heptyl and higher saturated alcohols ($C_8$ to $C_{20}$).

Beta(2)-alkyl-substituted primary monohydric (normal) alcohols or alkanols ($C_5$–$C_{18}$), which are reacted with alkylmagnesium halide compounds in various embodiments of this invention, and which surprisingly are hydrocarbon soluble, are exemplified by 2-methyl-1-pentanol, 2-methyl-1-butanol, 2-ethyl-1-butanol, 2-ethyl-1-pentanol, 2-ethyl-1-hexanol, 2-ethyl-4-methyl1-pentanol, 2-propyl-1-heptanol, 2-methyl-1-hexanol, 2-ethyl- 5-methyl-1-octanol, 2,2-dimethyl-1-octanol, and the like, or mixtures thereof. Particularly important beta(2)-alkyl-substituted primary monohydic normal alcohols are 2-methyl-1-pentanol and 2-ethyl- 1-hexanol and mixtures thereof.

Beta-alkylsubstituted $C_5$-$C_{18}$ acyclic secondry alcohols; i.e., those secondary alcohols bearing at least one $C_1$-$C_4$ alkyl branch at the carbon atom beta to the hydroxyl group, which are reacted with alkylmagnesium halide compounds to make hydrocarbon soluble products of this invention are are exemplified by 2-methyl-3-pentanol, 2,2-dimethyl-3-pentanol, 2,4-dimethyl -3-pentanol, 3-methyl-2-pentanol, 3-methyl-2-butanol, 4-methyl-3-hexanol, 3-methyl-2-hexanol, 2,4-dimethyl3-hexanol, 3,4-dimethyl-2-hexanol, 2,4-dimethyl-3-hebtanol, 4methyl-3-heptanol, 2-methyl-3-octanol, 2,2-dimethyl-3octanol, and the like. Also contemplatedare beta-alkyl-substituted cyclic $C_6$-$C_{18}$ secondary alcohols such as 2-methylcyclopentanol, 2-methylcyclohexanol, 2,6-dimethylcyclohexanol, 2-tert-butylcyclohexanol, and the like. Most preferred are those cyclic secondary alcohols bearing at least two beta methyl groups or one beta-tert-butyl group relative to the hydroxyl moiety.

Beta-alkylsubstituted $C_6$-$C_{18}$ cyclic or acyclic tertiary alcohols; i.e., those tertiary alcohols bearing at least one $C_1$-$C_4$ alkyl branch at the carbon atom beta to the hydroxyl group which are reacted with alkylmagnesium halide compounds to make hydrocarbon soluble products of this invention are exemplified by 2,3-dimethyl-2-butanol, 2,3-dimethyl-2-pentanol, 2,3-dimethyl -3,-pentanol, 2,3-dimethyl-2-hexanol, 3,4-dimethyl-4-heptanol, 2,3,4-trimethyl-3-pentanol, 3,4,4-trimethyl-3-hexanol, 1,2-dimethylcyclopentanol, 1,2,6-trimethylcyclohexanol, and the like.

Other, less preferable $C_6$-$C_{18}$ secondary and tertiary cyclic and acyclic alcohols which are reacted with alkylmagnesium halide compounds in a further embodiment of hydrocarbon soluble products of this invention are those alcohols bearing alkyl group substitution further than the beta position from the carbon atom bearing the hydroxyl group; e.g., on the gamma or delta carbons. Examples of such alcohols are 4-methyl-2-pentanol, 5-methyl-3-hexanol, 2,6-dimethyl-4-heptanol, 2-methyl-4-octanol, 3,5-dimethyl-3-hexanol, 2,6,8-trimethyl-4-nonanol, and3-methylcyclohexanol.

Aromatic alcohols ($C_6$-$C_{20}$) which are reacted with alkylmagnesium halide compounds in various embodiments of this invention are exemplified by phenol, benzyl alcohol, 2-tertiary-butyl phenol, alpha and beta napthol, ortho, meta, and para cresols, 1-phenylcyclohexanol, 2-phenylphenol, diphenylmethanol, 2-indanol, 2-phenylethanol, 3-phenyl-1-propanol, 2,6-dimethyl phenol, iso-eugenol, 2,4,6-trimethylphenol, and the like.

Typical examples of the hydrocarbyloxymagnesium halides of this invention are ethoxymagnesium chloride, n-butoxymagnesium chloride, 2-methylpentyloxymagnesium chloride, 2-ethylhexyloxymagnesium chloride, 2-methylbutoxymagnesium chloride, n-propyloxymagnesium bromide, phenoxymagnesium chloride, etc.

The magnesium metal used in the process of this invention can be in powder, chip or granular form. Magnesium metal stored for more than 6 months or exposed to air produces blackish product containing unreacted magnesium metal. Clean freshly produced magnesium metal, but without activation with iodine, produces, while suitable, a dark-grayish product containing more than 0.1% free unreacted metal. U.S. Pat. No. 2,287,088 discloses that suitable activators for alkaline earth metals such as calcium and magnesium are aluminum, mercuric salts, iodine or anhydrous stannic chloride. Iodine is preferred in the present process as it is effective in very small amounts. Activation with iodine is conducted between about 50° to about 200° C., preferably from about 70° C. to about 120° C. in refluxing hydrocarbon solvent for 1 to 4 hours using a maximum of up to 1 gram of iodine per mole of magnesium. The amount of iodine used for activation of the magnesium is dependent on the size (exposed surface area) of magnesium metal. Fine powder, about-200 sieve (75 m), (ASTM E-11) needs about 0.5 grams of iodine per mole of magnesium metal, whereas chips need about 0.2 grams of iodine per mole of magnesium metal. The magnesium metal after activation with iodine can be washed in hydrocarbon solvent before the first reaction step, but washing is not critical.

The hydrocarbon reaction medium can be any aprotic hydrocarbon that is inert to the reaction. It is preferred that the hydrocarbon solvent be aliphatic, alicyclic or aromatic and have the same or a higher boiling point than the boiling point of the oxygen containing compound. The hydrocarbon solvent used can be selected from n-hexane and n-heptane, cyclohexane, methylcyclohexane, benzene, toluene, isoparaffinic hydrocarbon fractions such as Isopar E ™, Isopar G ™ or Isopar H ™ and other commonly used inert hydrocarbon solvents. The Isopar materials are isoparaffinic solvents whose characterizing properties are set forth in Table 2 below.

The alkyl halide used has the formula RX where X is halide, preferably chloride, and R is a radical of 1 to 20 carbon atoms, preferably an alkyl, of 1 to 8 carbon atoms or aryl or cycloalkyl radical of 3 to 8 carbon atoms, such as ethyl chloride, butyl chloride, cyclohexyl chloride, and benzyl chloride.

In accordance with one aspect of the present invention there is provided a process for producing a hydrocarbyloxymagnesium halide by reacting an alkylmagnesium halide in an inert hydrocarbon solvent with an oxygen containing compound preferably an anhydrous alcohol slowly with reasonably good agitation while maintaining the temperature of the reaction mixture between 50° C. and the refluxing temperature of the hydrocarbon medium. The reaction mixture is agitated, preferably at the hydrocarbon refluxing temperature, for about 2 to 4 hours to complete the reaction. The mixture is filtered to obtain solid hydrocarbyloxymagnesium chloride. The filtered product may be then dried under reduced pressure at 55° to 95° C. to remove entrained solvents; optionally, the reaction slurry may be spray dried to obtain a granular type of dry hydrocarbyloxymagnesium halide or physically processed by other means to obtain a dry product of the desired type. The resulting solvent free, dry, solid hydrocarbyloxymagnesium halide products have RO/Mg/X molar ratios of about 1:1:1. The Applicant has discovered that by reacting an alkylmagnesium halide with an oxygen containing compound a hydrocarbyloxymagnesium halide is produced whereas the prior art process of reacting magnesium metal simultaneously with an alkyl halide and an oxygen containing compound produces essentially magnesium dialkoxides (See comparative Example A).

In accordance with another aspect of the present invention, there is provided, hydrocarbon soluble hydrocarbyloxymagnesium halides. To the product obtained by reacting the magnesium metal and alkyl halide, there is added a 2-alkyl substituted oxygen containing compound such as alcohols, ketones, aldehydes or esters in the range of 1.1 to 2.0 moles per mole of magnesium to form a soluble hydrocarbyloxymagnesium halide in hydrocarbon solvent. The reaction of the alkylmagnesium halide with the oxygen containing compound can be carried out at between ambient and the reflux temperature of the hydrocarbon solvent. Surprisingly, the resulting hydrocarbyloxymagnesium halides are soluble in hydrocarbon solvents; these hydrocarbyloxy compounds have more than 1 molar concentration of magnesium and an RO/Mg/X molar ratio equal to about 1:1:1. Solid hydrocarbon insoluble hydrocarbyloxymagnesium halide, such as ethoxymagnesium chloride having RO/Mg/X molar ratio of about 1:1:1, are solubilized in hydrocarbon solvent (n-heptane) by the addition of a 2-alkyl substituted oxygen containing compound such as 2-methyl-1-pentanol, or 2-ethyl-1hexanol, in the range of 1.2 to 1.4 moles per mole of magnesium of the hydrocarbyloxymagnesium halide. The soluble product obtained has higher than one mole of magnesium concentration and an RO/Mg/X molar ratio of 1:1:1.

In accordance with a third aspect of the present invention, there are provided low melting alkoxy-magnesium halides. To an alkylmagnesium halide slurry, an oxygen containing compound such as 2-methyl-1-pentanol was added in an amount sufficient to provide 1.3 moles of alcohol per mole of magnesium; the alcohol is added slowly while the temperature is maintained between 40° C. and 90° C. The slurry is then filtered to remove any suspended particles. The clear filtrate is then evaporated under reduced pressure at 90° C. until no further solvent is recoverable. On heating further to above 100° C., the solid mass turns into a viscous fluid but no more solvent can be recovered. On cooling, this viscous fluid turned into a hard, glassy solid. The melting range of these products were found to be between 100° and 120° C. On analysis of these products, the RO/Mg/Cl molar ratios were found to be about 1:0.8:1.2. This indicates that low melting hydrocarbyloxymagnesium halides can be produced with or without variation in the RO/Mg/Cl molar ratios.

The process can use magnesium metal powder, granular magnesium or magnesium chips as the source of magnesium. The magnesium is preferably activated in an inert hydrocarbon solvent in the presence of a small amount of iodine (0.1 to 0.5 grams of iodine per mole of magnesium metal). Activation is carried out by heating the hydrocarbon solvent containing the iodine and magnesium metal, suitably, at the reflux temperature of the hydrocarbon selected, for about 60 to about 120 minutes. Then in the first step, an alkyl halide, RX, or a mixture of alkyl halides, where R is an alkyl group containing 2 to 18 carbon atoms, as such or diluted in hydrocarbon solvent, is then added gradually to the activated metal-hydrocarbon slurry. The magnesium metal with alkyl halide reaction is carried out at reflux temperature and allowed to reflux for about 2 hours to complete the reaction.

FIGS. 1 and 2 are C-13 NMR (CP/MAS) spectra of the product of Example 1 and comparison examples A and B. FIG. 1, Spectrum A, relates to Comparison Example B; FIG. 1, Spectrum B, relates to Example 1 of this invention; and FIG. 2, Spectrum C, relates to Comparison Example A. The spectra show that the product of Example 1 differs significantly from the products of Comparison Examples A and B.

The following examples further illustrate the present invention. All reactions were conducted in an inert, argon atmosphere under anhydrous conditions.

Example 1, Solid Hydrocarbyloxymagnesium Halide ROMgX

A reactor equipped with a reflux condensor was charged under an argon atmosphere with 24.3 grams of magnesium metal (1 mole), 700 ml of n-heptane and 0.5 grams of iodine crystals. This mixture was heated to reflux temperature (98° C.) for 100 minutes to activate the metal. Then 93.0 grams (1 mole) of n-butyl chloride was added over about 25 minutes to this metal slurry at reflux temperature, the resulting reaction mixture was allowed to reflux for 120 minutes. Anhydrous ethyl alcohol (46 grams, re: 1 mole) was then slowly added drop-wise under good agitation. The alcohol addition was completed in one hour. The temperature of the reaction slurry was maintained between 70° C. and the temperature of the refluxing hydrocarbon. The reaction slurry was stirred at the hydrocarbon reflux temperature for 4 hours. The reaction slurry was filtered to collect solid product, which was dried under vacuum at 65° C. Analysis of the dry, powdery, solvent free ethoxymagnesium chloride showed 22.6% total magnesium, 33% chloride and 41.3% $OC_2H_5$ (total base), which is a product having an RO/Mg/X molar ratio equal to 1:1:1.

This example was repeated several times. The time the slurried final product was stirred at the reflux temperature was varied from 1 to 4 hours with substantially the same results.

Comparative Example A

The raw materials, parameters and procedures used in Japanese patent application (Kokai-Sho No. 57-151601) were followed to produce the same product.

2.32 g of magnesium metal was placed in a flask with 150 ml of n-heptane and 0.06 g of iodine. A mixture of 6.6 ml of ethanol and 11.8 ml of n-butyl chloride was added drop by drop over one hour at 70° C. The mixture was then stirred for six hours at 95° C. until the unreacted metal had disappeared. The solid product was filtered and dried at 65° C. under reduced pressure to remove entrained solvents.

The product obtained had some alkyl group ($C_4H_9$) attached to magnesium and the product as mentioned in the patent had a Cl/Mg molar ratio of 0.60 instead of 0.52. Recovery of metal as product was good. It was observed that when activated magnesium metal, n-butyl chloride and alcohol were mixed together and heated up to a reflux temperature of 70° C., no alkane was released for several hours which indicated that the butyl chloride did not react with the magnesium metal in the presence of alcohol at the temperature of 70° C. in heptane. Most of the alcohol reacted with magnesium initially to form magnesium diethoxide [Mg(OEt)$_2$], and some butyl chloride reacted with magnesium and the ultimate product was found to be mainly Mg(OEt)$_2$ with some MgCl$_2$ and BuMgCl. Almost half of the chloride added as butyl chloride was left unreacted.

Comparative Example B Preparation of Solid Magnesium Diethoxide Mg(OEt)$_2$ 24.3 gm of magnesium metal (1 mole) was placed in a 3-necked round bottom reaction flask along with 600 to 700 ml of n-heptane. 0.5 gm of iodine crystals were added to the metal-heptane slurry. This mixture was heated to reflux temperature (98° C.) for about 90 minutes to activate the metal under argon gas atmosphere. 101 gm (2.2 mole) of absolute ethyl alcohol was added slowly under agitation at reflux temperature. Alcohol addition was completed in 90–120 minutes. The temperature of the reaction slurry was maintained at refluxing temperatures of the solvent (70° C. to 98° C.). The reaction slurry was stirred for an additional 120 minutes. The reaction slurry was filtered to collect solid product. The filtered solid product was then dried under reduced pressure at 65° C. to remove entrained solvents. The resulting dry solid magnesium diethoxide analysis showed 21.7% total magnesium, 40.63% carbon, 8.8% hydrogen. Trace element analysis and C-13 NMR (CP/MAS) of this product were carried out.

The similarities and differences between the solid products from Example 1 and Comparison Examples A and B were established by carbon-13 nuclear magnetic resonance utilizing cross polarization and magic angle spinning [C-13 NMR (CP/MAS)] spectra studies. The spectroscopic studies started with the magnesium diethoxide of Comparison B and in the study this spectra and compound were labeled (a). The product of Example 1 of the present invention, ethoxymagnesium chloride, is labeled (b) and the product of Comparison Example A, a magnesium catalytic component is labeled (c). All three products studied were solids.

The C-13 CP/MAS spectra of (a) $Mg(OEt)_2$, (b) EtOMgCl and (c) magnesium catalytic component product were made under identical conditions. In each spectra, each peak represents a distinct carbon environment, with the —$CH_2$— group around 60 ppm and the —$CH_3$— group near 20 ppm. Spectrum (b) of ethoxy magnesium chloride showed that it is possible that ethoxymagnesium chloride (b) contains a very small amount of $Mg(OEt)_2$, but a minimum of six distinct methyl groups and three distinct methylene groups along with several other ethyl groups present in greater stoichiometry. EtOMgCl product is unique and cannot be a simple mixture of $Mg(OEt)_2$ and $MgCl_2$. Spectrum (c) of magnesium catalytic product of Kokai Patent appears to be rather pure $Mg(OEt)_2$. The two peaks agree within acceptable error limits with the recorded spectrum (a) of $Mg(OEt)_2$. Small signals around the base of the major peaks in spectrum (c) account for a few percent of the total intensity which may be due to the presence of EtOMgCl and/or BuMgCl. Copies of the spectra appear below in FIGS. 1 and 2.

From the C-13 NMR study of the above three products, it can be concluded that (i) EtOMgCl (b) is not a mixture of $Mg(OEt)_2$ and $MgCl_2$; (ii) the magnesium catalytic component product of Comparison Example A has no similarity to EtOMgCl (b) and that the product of Comparison Example A is very similar to $Mg(OEt)_2$.

Example 2, Ethoxymagnesium Chloride:Solid (EtOMgCl)

Example 1 was repeated using 1.505 moles of magnesium metal, as a fine powder (granular) which was reacted (after iodine-activation) with 1.582 moles of alkyl halide and followed by 1.621 moles of anhydrous ethanol; the final dry powdery product obtained analyzed 22.00% total Mg, 38.71% $C_2H_5O$- moiety (total base) and 33.65% Cl and had no traceable metal particles. The solid product was analyzed by GLC to determine the presence of free (unreacted) ethanol (solvated) and none was found, indicating that no free $MgCl_2$ was present.

Example 3, Methoxymagnesium Chloride: Solid (MeOMgCl)

Following the procedure of Example 1, 12.16 gm of magnesium metal powder (0.5 mole) was placed in a one liter 3 necked reactor along with 500 ml of n-heptane and 0.15 gm iodine crystals. The mixture was heated under an argon atmosphere to reflux (98°) for about 90 minutes. 53 ml of n-butyl chloride (0.505M) was then gradually added at reflux over 20 minutes. The reaction slurry was allowed to react at reflux (93°–95° C.) for 90 minutes. 16.5 gm, 20.8 ml (0.51m) of methyl alcohol 99.9+% was added drop by drop to the reaction slurry over about 30 minutes. The reaction was continued for another 90 minutes at reflux temperature. The slurry was filtered and washed with pentane (one time) to remove excess entrained solvents. The filtered product was then dried at 60° C. under reduced pressure until no further solvent could be removed. The dried solid powdery product was analyzed, and found to contain 26.75% wt. Mg, 39.20% wt. Cl, and 33.81% wt $CH_3O$-moiety (total base), with 99.7+% purity.

Example 4, Butoxymagnesium Chloride: Solid (BuOMgCl).

Following the procedure of Example 1, 24.3 gms of magnesium metal (1.0 moles) in about 1 liter of n-heptane was activated with 0.25 gm iodine for about 120 minutes at reflux temperature. This magnesium was reacted then with 92.5 gm n-BuCl (1M) at reflux temperature for two hours. Then 92 ml of butanol was added to the reaction slurry very slowly with agitation and then allowed to react at reflux temperatures for two hours to complete the reaction. Solid product was filtered and dried under reduced pressure at 65° C. The final dried priduct contained 17.80% Mg, 25.96% Cl and 53.24% $C_4H_9O$- moiety (total base).

Results: (1) The product obtained by using 1:1:1 mole ratios of magnesium metal/n-BuCl/Butanol has RO/Mg/X molar ratios equal to 1:1:1 and has no traceable free unreacted metal. (2) Product had good filterability and gray white color.

Example 5, 2-Methylpentyloxymagnesium Chloride: Solid (2MPOMgCl)

Following the procedure of Example 1, 24.3 gm of magnesium metal chips were placed in a 3 necked 3 liter reactor with 0.25 g $I_2$ crystals and 1500 ml of Isopar G solvent. A fraction of isoparaffinic hydrocarbons (Isopar G) having a boiling range of 157° to 176° C. The magnesium was iodine-activated by heating under argon and at reflux for 90 minutes. The activated magnesium metal slurry in Isopar G was then reacted with 104 ml of n-butyl chloride (1M) at the solvent reflux temperature. After two hours of reaction, 125 ml of 2-methyl-1-pentanol was added slowly with good agitation. The thick reaction slurry was agitated at reflux for two hours. Because of the viscous nature of the thick slurry, it was difficult to filter when it was hot. Therefore, the solvent was removed under reduced pressure at 90°–100° C. The dried solid obtained was not a powder, but sticky gray flakes. Dried product was analyzed and found to contain 15.21% Mg; 58.95% $C_6H_{13}O$— moiety (total base) and 22.9% chloride. Free Mg metal was found to be less than 0.1% by wt. The product obtained, by using 1:1:1 mole ratios of magnesium metal, n-butyl chloride and 2-methyl-1-pentanol had a RO/Mg/X mole ratio very close to 1:1:1.

Example 6, 2-Methylpentyloxymagnesium Chloride (Soluble and Solid) (2-MPOMgCl)

Following the procedure of Example 1, 24.31 gm of magnesium metal powder (1.0 mole) was placed in a 3-necked 3 liter reactor flask, along with 1600 ml of isoparaffinic solvent (Isopar E) having a boiling range of 116°–139° C. and 0.25 gm of iodine crystals. This mixture was heated under an argon atmosphere to reflux temperature for about 60 minutes for metal activation. 105 ml of n-butyl chloride (1.0M) was then gradually added to the reaction slurry in 40 minutes, then reaction was continued for two hours at reflux temperature. Addition of 180 ml (1.4 moles) of 2-methyl-1-pentanol to the reaction slurry was started. The reaction slurry became thick and viscous at reflux temperatures when 60 ml of the 180 ml of the 2-methyl-1-pentanol was added. At this point the reaction slurry was cooled down to 65° C. At 65° C. the remaining 120 ml of 2-methyl-1-pentanol was added along with 400 ml of solvent (Isopar E) with good agitation to reduce the viscosity of the slurry. The 2-methyl-1-pentanol reacted with BuMgCl as was evidenced by the release of butane. Butane was distilled off through reflux condensor to maintain the reaction temperature close to the reflux temperature of solvent Isopar E. The reaction was continued for two hours. The slurry was filtered while hot, 90°–100° C. The filtration rate was fast and complete in about 10–15 minutes. Final volume of filtrate was about 2100 ml. Fine gray suspended particles as solid were collected on the filter. The clear filtrate was analyzed and found to have 0.435 molar magnesium concentration with 91.40+% magnesium recovery. This filtrate was found to be stable at 0° to 40° C. on storage.

The clear filtrate was then concentrated under reduced pressure at 80° C. to half of its original volume. Concentrated filtrate was then analyzed and found to have 0.95 molar total magnesium concentration and 0.44 molar magnesium was present as $Mg(OR)_2$ and 0.51 molar Mg was present as $MgCl_2$. The 0.954 molar solution of this product was a thin, clear liquid and found to be very stable (without change of viscosity) between 0° to 40° C. on storage. This test work has clearly indicated that hydrocarbon soluble hydrocarbyloxymagnesium chloride having a 1.0 molar concentration can be obtained without use of any aluminum or titanium solubilizing compounds.

Example 7, 2-Methylpentyloxymagnesium Chloride: Solid (2MPOMgCl)

Part of the concentrated filtrate (0.95 moles, 500 ml) of Example 6 was concentrated further under reduced pressure at 90° C. No solid formation was found until 200 ml of solvent was recovered; this indicated that a soluble product up to 2 to 2.5 molar concentration could be made. On further concentration the liquid turned viscous and thicker. Stripping of the solvent at 90°–100° C. was continued until no solvent or 2-methyl-1-pentanol could be removed. The product in the flask became an almost "gum-like", type thick sticky fluid. Heating was raised to 110° C. for three hours to recover very little solvent (2–3 ml). Then, the product became a glassy clear solid on cooling to room temperature. This solid product was scraped from the concentration flask and analyzed for its components, and found to contain 11.43% Mg, 18.1% Cl, 44.2% $C_6H_{13}O$- moiety (total base), and remaining was solvation of excess alcohol and traces of hydrocarbon solvent.

Example 8, Low Melting Alkoxymagnesium Halides: Solid ROMgx

Upon heating, the clear solid glassy product from Example 7 melted over a range of 110°–120° C. This indicated that 2-methylpentyloxymagnesium chloride having alcohol of solvation may be used as a low melting hydrocarbyloxymagnesium halide.

Since hydrocarbon soluble 2-methylpentyloxymagnesium chloride can be made using excess of 2-methyl-1pentanol, other solid hydrocarbyloxymagnesium chloride in heptane or other hydrocarbon solvents were solubilized by adding to it more than 1 mole of a 2-alkyl-substituted alcohol per mole of magnesium where heptane was used as solvent and reaction was carried out at 40°–60° C. Results are shown in Table 1.

Test: 16.0 gm (0.153 moles) of EtOMgCl was slurried in 250 ml of n-heptane and added to it was 26 ml (0.206M) of 2-methyl-1-pentanol at 63° C. Reaction or solvation was seen instantly and within 15 minutes the solid was dissolved. Reaction liquid containing suspended fine gray particles was filtered to obtain a clear solution. The filtrate was analyzed and found to contain 0.6 molar magnesium concentration. The filtrate was concentrated, by stripping out some of the heptane and ethanol, under reduced pressure at 65° C. The concentrated solution was found to contain 1.2 moles concentration of magnesium, 0.59 moles of magnesium as $MgCl_2$ and 0.61 moles of magnesium as alkoxide.

TABLE 1

| Hydrocarbon Soluble Alkoxymagnesium Chlorides | | | |
|---|---|---|---|
| | Alcohols (1.35 M per Mole of Magnesium) | | |
| Start Material | 2MPOH (a) | 2EHOH (b) | 2MBOH (c) |
| Solid EtOMgCl + heptane | Soluble | Soluble | Soluble |
| Solid MeOMgCl + heptane | Soluble | Soluble | Soluble |
| Solid BuOMgCl + heptane | Soluble | Soluble | Soluble |
| Solid 2MPOMgCl + heptane | Soluble | Soluble | Soluble |

(a) 2MPOH = 2-methylpentyl alcohol
(b) 2EHOH = 2-ethylhexyl alcohol
(c) 2MBOH = 2-methylbutyl alcohol

TABLE 2

| Isoparaffin Fractions - Typical Properties | | | |
|---|---|---|---|
| | Density | Distillation Range ° C. | Total Aromatics |
| (a) | 15° C. | I.B. Pt    F.B. Pt | (Volume %) |
| Isopar E ™ | 0.721 | 116    135 | 0.01 |
| Isopar G ™ | 0.749 | 155    175 | 0.02 |
| Isopar H ™ | 0.760 | 171    191 | 0.02 |

(a) Products of Exxon Chemical Co.

Example 9, Phenoxymagnesium Chloride - Solid (PhOMgCl)

A reactor equipped with a reflux condenser was charged under an argon atmospher with 6.55 gm of magnesium metal powder (0.269 moles), 250ml. of Isopar "E" isoparaffinic hydrocarbon solvent and a few crystals (0.2 gm) of iodine. This mixture was heated to reflux temperature (121° C.) for about 60 minutes to activate the metal. Then, 28.0 ml (0.27 moles) of n-butyl chloride was added in 30 minutes to this metal slurry at reflux temperature; the resulting reaction mixture was allowed to reflux for 90 minutes. Anhydrous crystalline phenol ($C_6H_5OH$) 28 gm (0.298 moles) was then added slowly in melted form along with Isopar E solvent (50°

C.) under good agitation. The phenol addition was completed in 20 minutes. During addition of phenol, heating was cut off and maintained at the reflux of released butane from the reaction. The reaction slurry turned from a grayish to a whitish color. The reaction slurry was then heated up to 90° C. with distillation of the refluxing butane. The slurry color turned from gray to white with no visible metal particles. Reaction was continued at 90° C. for another two hours with the addition of another 12 gms (0.128 moles) of phenol. The second addition of phenol was to see if any magnesium solubilized. The hot reaction slurry was then filtered to collect solid product. The solid product was washed with pentane to remove leftover solvents. The filtrate was tested for magnesium and found to be nil. The solid was dried under argon pressure until it was found to be a free flowing powder. Analysis of the solid white product showed 14.82% total magnesium, 56.78% $C_6H_5O$, 21.27% Cl, and remaining is free solvent. The filtrate was found to have all the excess phenol in it. This solid white product had an RO/Mg/X (i.e., $C_6H_5O$/Mg/Cl) molar ratio almost equal to 1:1:1.

Example 10, 2-methyl-1-pentyloxymagnesium chloride Soluble $2MPO_{(2-n)}MgCl_n$

Magnesium powder 6.65 gm, (0.273 moles) along with 225.0 ml Isopar "H" hydrocarbon solvent and 0.20 gm of iodine crystals were placed in a 3-necked reaction flask under an argon atmosphere. This mixture was heated under the argon atmosphere to 145° C. for about 60 minutes for metal activation. n-Butyl chloride (40 ml, 0.385 moles) was then gradually added to the reaction slurry in 30 minutes. The heating was cut off due to exothermic reaction and reflux. The reaction of the slurry was continued for about two hours at reflux temperature. The reflux temperature during this period dropped to about 110° C. The reflux solvent contained alkenes (i.e., butene/octene, etc.). After two hours of reaction, heating was cut off and then, the first 15 ml of 2-methyl-1-pentanol of a total of 60 ml was added drop by drop to the reaction slurry. On addition of this alcohol, butane was released with exothermic reaction and the slurry turned into a thick gum-like gel. When the temperature dropped to about 50° C., the remaining 45 ml of 2-methyl-1-pentanol, along with 50 ml of Isopar H solvent, was added quickly under good agitation to reduce the viscosity of the slurry. The 2-methyl-1-pentanol reacted with BuMgCl as was evidenced by the release of butane. The reaction fluid containing some grayish particles was heated slowly with reflux. The reflux butane with some alkene, such as butene/octene, was distilled off through the reflux condenser to increase the reaction temperature close to 145° C. It is important to keep the temperature two to three degrees lower than 2-methyl-1-pentanol's reflux temperature (148° C.–150° C.). The reaction was continued at 145° C. for about 30 minutes. The reaction slurry was filtered while hot (90° C.–120° C.). The filtration was fast and completed in about ten minutes. Final volume of the filtrate was about 340 ml. Fine gray suspended particles of solid were collected on the filter. The clear filtrate was analyzed and found to have a 0.79 molar magnesium concentration with about 98% magnesium recovery. The detailed analysis of the liquid product was found to be 0.79 moles magnesium, 0.50 moles 2MPO (as total base), 1.08 moles chloride per liter, along with solvent Isopar H and excess 2-methyl-1-pentanol. The product formula can be presented as $$RO_{0.633}Mg_{1.0}Cl_{1.367}$$

This soluble 0.79 molar magnesium product generated some precipitation of solid below 20° C. Therefore, 30 ml of 2-methyl-1-pentanol (0.24 moles) was added to solubilize the solid to make the solution stable at lower temperatures. This example has indicated that to obtain a stable solution product of $(RO)_{2-n}MgCl_n$ where $n > 1$, in hydrocarbon solvent between 0° C. to 40° C., the alcohol (2-alkyl substituted) requirement is between 1.4 to 3.0 mole per mole of magnesium.

Example 11, Solid Ethoxymagnesium Chloride

A reactor equipped with a reflux condenser was charged under an atmosphere of argon gas with 24.3 grams of magnesium metal (1 mole), 700 ml of n-heptane and 0.5 grams of iodine crystals. This mixture was heated to reflux temperature (98° C.) for 100 minutes to activate the metal. Then 93.0 grams (1 mole) of n-butyl chloride was added over about 25 minutes to this metal slurry at reflux temperature, the resulting reaction mixture was allowed to reflux for 120 minutes. Anhydrous ethyl alcohol (46 grams, re: 1 mole) was then slowly added drop-wise under good agitation. The alcohol addition was completed in one hour. The temperature of the reaction slurry was maintained between 70° C. and the temperature of the refluxing hydrocarbon. The reaction slurry was stirred at the hydrocarbon reflux temperature for 4 hours. Part of the reaction slurry was filtered to collect solid product, which was dried under vacuum at 65° C. Analysis of the dry, powdery, solvent free ethoxymagnesium chloride showed 2.6% total magnesium, 33% chloride and 41.3% $OC_2H_5$ (total base), which is a product having an RO/Mg/X molar ratio equal to 1:1:1.

Comparative Example C

The remainder of the reaction slurry from Example 11, 250 ml, was left in the reaction flask to which was added 15 milliliters of ethyl alcohol. This slurry was agitated at reflux for one hour and then cooled to room temperature. A clear liquid recovered by decantation was analyzed for magnesium but none was found. This test work demonstrates that hydrocarbon solubility of the hydrocarbyloxy halide depends on the use of a 2-substituted oxygen containing compound. This result is to be compared with the results of Example 8.

Example 12, Solid n-Propoxymagnesium Chloride

Example 11 was repeated using one mole of anhydrous n-propyl alcohol to replace the one mole of anhydrous ethyl alcohol used in Example 11. A solid reaction product, n-propoxymagnesium chloride, was recovered from part of the reaction slurry and identified.

Example 13, Solid n-Butoxymagnesium Chloride

Example 11 was again repeated using one mole of anhydrous n-butyl alcohol to replace the one mole of anhydrous ethyl alcohol used in Example 11. A solid reaction product, n-butoxymagnesium chloride, was recovered from part of the reaction slurry and identified.

Comparative Example D

The remainder of the reaction slurry from Example 12, about 250 ml, was left in the reaction flask to which was added 15 milliliters of anhydrous n-propyl alcohol. This slurry was agitated at reflux for one hour then cooled to room temperature. A clear liquid recovered by decantation was analyzed for magnesium but none was found.

Comparative Example E

The remainder of the reaction slurry from Example 13, about 250 milliliters, was left in the reaction flask to which was added 15 milliliters of anhydrous n-butyl alcohol. This slurry was agitated at reflux for one hour then cooled to room temperature. A clear liquid recovered by decantation was analyzed for magnesium but none was found.

Examples 10, 11 and 12 and comparative Examples C, D and E demonstrate that hydrocarbon solubility of the hydrocarbyloxymagnesium halide depends on the use of a 2-substituted oxygen containing compound. The results of comparative Examples C, D and E demonstrate that solid hydrocarbyloxymagnesium chlorides made from normal alcohols are not hydrocarbon soluble in the presence of an excess of the normal alcohol. The results of these comparative examples are to be compared to Example 8 where use of excess 2-substituted alcohol results in a hydrocarbon soluble composition.

What is claimed is:

1. A process for making solid organometallic hydrocarbyloxymagnesium halides comprising:
   (a) reacting activated magnesium metal with an alkyl hlaide of the formula R'X, in which R' is a radical containing 1 to 20 carbon atoms, in a dry inert hydrocarbon medium, under a dry inert atmosphere at a temperature of at least 40° C. to produce a compound of the formula R'MgX in which R' and X have the meanings ascribed to them herein; and,
   (b) reacting the R'MgX compound with at least one mole of a monohydric alcohol of the general formula ROH wherein R is an alkyl, aryl, cycloalkyl or alkylaryl group containing 1 to 18 carbon atoms per mole of magnesium metal at a temperature of at least 40° C. to produce an ether free compound ROMgX in which R is an alkyl group of 1 to 18 carbon atoms.

2. The process of claim 1 wherein the magnesium metal is activated by heating the magnesium metal in the hydrocarbon solvent containing 0.1 to 1 gram of iodine per mole of magnesium metal at a temperature of 50° to 200° C. for one to four hours.

3. The process of claim 1 wherein the dry inert gas is nitrogen or argon.

4. The process of claim 1 wherein the alcohol is selected from methanol, ethanol, propanol, isopropanol, butanol, isobutanol, octanol, hexanol and cyclohexanol.

5. The process of claim 1 wherein the alcohol is a 2-alkyl substituted primary alcohol selected from 2-methyl-1-pentanol, 2-ethyl-1-butanol, 2-ethyl-1-pentanol, 2-ethyl-1-hexanol, 2-ethyl-4-methyl-1-pentanol, 2-methyl-1-hexanol, 2-propyl-1-heptanol, 2-ethyl-5-methyl-1-octanol or mixtures thereof.

6. The process of claim 1 wherein hydrocarbon soluble hydrocarbyloxymagnesium halide is made using 2-alkyl substituted alcohols in the range of 1.1 to 2.0 moles per mole of magnesium.

7. The process of claim 1 wherein hydrocarbon soluble hydrocarbyloxymagnesium halide is made using ethoxy, butoxy or methoxymagnesium halide with a 2-alkyl substituted alcohol.

8. A hydrocarbon soluble hydrocarbyloxymagnesium halide of the formula ROMgX wherein R is a primary 2-alkyl substituted radical of 5 to 18 carbon atoms and X is halide.

9. The hydrocarbyloxymagnesium chloride of claim 11 wherein the primary two alkyl substituted radical is selected from the group consisting of 2-methyl-1-pentyl, 2-ethyl-1-butyl, 2-ethyl-1-pentyl, 2-ethyl-1-hexyl, 2-ethyl -2-methyl-1-pentyl, 2-methyl-1-hexyl, 2-propyl-1hexyl and 2-ethyl-5-methyl-1-octyl.

10. The process of claim 1 in which the inert hydrocarbon medium is selected from n-hexane and n-heptane, cyclohexane, methylcyclohexane, benzene, toluene and isoparafinnic solvents.

11. A hydrocarbon solution of a hydrocarbyloxymagnesium halide of the formula ROMgX in which R is a primary 2-alkyl substituted radical of 5 to 18 carbon atoms and X is a halide and which solution contains at least 0.1 mole of excess precursor of the 2-alkyl substituted radical.

12. A process for the production of organometallic hydrocarbyloxymagnesium halides of the formula ROMgX comprising:
   (a) reacting, in a dry inert hydrocarbon medium, activated magnesium metal with an alkyl halide of the formula R'X', in which R' is a redical of 1 to 20 carbon atoms and X is a halide, in a dry inert atmosphere at a temperature of at least 40° C. to produce a compound of the formula R'MgX in which R' and X have the meanings ascribed to them herein, and,
   (b) reacting the R'MgX compound, in a dry inert hydrocarbon solvent, with 1.1 to 2.0 moles of a beta-alkyl substituted primary alcohol containing 5 to 18 carbon atoms per mole of magnesium to produce ether free beta-alkyl substituted hydrocarbyloxymagnesium halides.

13. The process of claim 12 wherein the beta-alkyl substituted alcohol is a 2-alkyl substituted primary alcohol selected from 2-methyl-1-pentanol, 2-ethyl-1-butanol, 2-ethyl-1-pentanol, 2-ethyl-1-hexanol, 2-ethyl-4-methyl-1-pentanol, 2-methyl-1-hexanol, 2-propyl-1-heptanol, 2-ethyl-5-methyl-1-octanol or mixtures thereof.

14. The process of claim 12 wherein hydrocarbon soluble hydrocarbyloxymagnesium halide is made using 2-alkyl substituted alcohol in the range of 1.35 to 2.0 moles per mole of magnesium.

15. A process for the production of a hydrocarbon soluble hydrocarbyloxymagnesium halide comprising reacting, in a dry hydrocarbon solvent in a dry inert atmosphere at a temeprature of at least 20° C., a solid, hydrocarbon insoluble hydrocarbyloxymagnesium halide, having a primary, unsubstituted, hydrocarbyloxy group of 1 to 20 carbon atoms, with 1.2 to 1.4 moles of a 2-alkyl substituted alcohol of 5 to 18 carbon atoms per mole of magnesium to produce the hydrocarbon soluble hydrocarbyloxymagnesium halide.

16. A process for the production of novel low-melting hydrocarbyloxymagnesium halide of the formula ROMgX wherein R is a beta-alkyl substituted group having 5 to 18 carbon atoms comprising:

(a) reacting, in a dry inert hydrocarbon medium, activated magnesium metal with an alkyl halide of the formula R'X, in which R' is a rdical of 1 to 20carbon atoms and X is a halide, in a dry inert atmosphere, at a temperature of at least 40° C. to produce a compound of the formula R'MgX in which R' and X have the meanings ascribed to them herein; and, (b) racting the R'MgX compound in a dry inert hydrocarbon solve, with 1.35 to 2.0 moles of a beta-alkyl substituted primary alcohol per mole of magnesium; and, (c) removing the solvent and said excess alcohol to produce a low melting solid product of the formula ROMgX containing between 1 to 1.3 moles of bta-alkyl substituted alcohol per mole of magnesium.

17. The process of claims 12, 15 or 16 wherein the dry inert atmosphere is selected from nitrogen or argon.

18. The process of claims 12, 15 or 16 wherein the beta-alkyl substituted primary alcohol is a 2-alkyl substituted primary alcohol of 5 to 18 carbon atoms.

19. The process of claims 12, 15 or 16 wherein the beta-alkyl substituted alcoholis a 2-alkyl substituted primary alcohol selected from 2-methyl-1-pentanol, 2-ethyl-1-butanol, 2-ethyl-1-pentanol, 2-ethyl-1-hexanol, 2-ethyl-4-methyl-1-pentanol, 2-methyl-1-hdxanol, 2-propyl-1-heptanol, 2-ethyl-5-methyl-1-octanol or mixtures thereon.

20. The process of claims 12, 15 or 16 wherein the dry inert hydrocarbon solvent is selected from n-hexane, n-heptane, cyclohexane, methylcyclohexane, benzene, toluene or isoparafinnic solvents.

21. Anèther-free hydrocarbyloxymagnesium halide comprising a compound of the formula ROMgX whrein RO is a primary beta-alkyl substituted hydrocarbyloxy radical of 5 to 18 carbon atoms.

22. The ether-free low melting hydrocarbyloxymagnesium halide of cliam 21 containing 0.1 to 0.3 moles excess of the hydrocarbyloxy radical precursor.

23. The ether-free hydrocarbyloxymagnesium halide of claim 21 containing at least 0.3 moles excess of the hydrocarbyloxy radical precursor and a solvating amount of a hydrocarbon solvent.

24. The process of claim 1, 12 or 16, wherein R' is a radical selected from methyl, ethylk propyl, isopropyl, butyl, isobutyl, octyl, hexyl an cyclohexyl.

* * * * *

UNITED STATES PATENT AND TRADEMARK OFFICE
CERTIFICATE OF CORRECTION

PATENT NO. : 4,792,640

DATED : December 20, 1988

INVENTOR(S) : Vijay C. Mehta

It is certified that error appears in the above-identified patent and that said Letters Patent is hereby corrected as shown below:

ON TITLE PAGE:

In the title, "Hydrocarbyloxy Magnesium Halides" should read --Hydrocarbyloxymagnesium Halides--. Column 1, line 7, "hydrocarbyloxy magnesium halides" should read --hydrocarbyloxymagnesium halides--. Column 1, line 51, "X' C(OR')hd" should read --X' $C(OR')_{4-m}$ --. Column 1, line 52, delete "4-m". Column 1, line 62, "an an" should read --and an--.

Column 2, line 50, "aldehydes or are" should read --aldehydes or esters are--. Column 3, line 3, "monohydic" should read --monohydric--. Column 3, line "are are exemplified" should read --are exemplified--. Column 3, line 14, "2,4-dimethyl3-hexanol" should read --2,4-dimethyl-3-hexanol--. Column 3, line 15, "hebtanol" should read --heptanol--. Column 3, line 16, "4methyl-3-heptanol" should read --4-methyl-3-heptanol--. Column 3, line 17, "3octanol" should read --3-octanol--; and "contemplatedare" should read --contemplated are--. Column 3, line 31, "dimethyl -3," should read --dimethyl-3 --. Column 5, line 19, "1hexanol" should read --1-hexanol--.

UNITED STATES PATENT AND TRADEMARK OFFICE
CERTIFICATE OF CORRECTION

PATENT NO. : 4,792,640

DATED : December 20, 1988

INVENTOR(S) : Vijay C. Mehta

It is certified that error appears in the above-identified patent and that said Letters Patent is hereby corrected as shown below:

Column 8, line 36
"priduct" should read --product--. Column 10, line 11, "1pentanol" should read --1-pentanol--. Column 10, line 57, "witha" should read --with a--; and line 58, "atmospher" should read --atmosphere--. Column 13, line 36, "hlaide" should read --halide--. Column 14, line 12, "claim 11" should read --claim 8--. Column 14, line 32, "redical" should read --radical--. Column 15, line 3, "rdical" should read --radical--; line 4, "20carbon" should read --20 carbon--; line 16, "bta-alkvl" should read --beta-alkyl--; and line 24, "alcoholis" should read --alcohol is--. Column 16, line 3, "hdxanol" should read --hexanol--; line 10, "Anether-free" should read. --An ether-free--; line 11, "whrein" should read --wherein--; line 15, "cliam" should read --claim--; line 22, "ethylk" should read --ethyl,--; and line 23, "an cyclohexyl" should read --and cyclohexyl--.

Signed and Sealed this

Twenty-eighth Day of January, 1992

*Attest:*

HARRY F. MANBECK, JR.

*Attesting Officer*     *Commissioner of Patents and Trademarks*